(12) United States Patent
Magno (10) Patent No.: US 11,937,842 B2
(45) Date of Patent: Mar. 26, 2024

(54) DETACHABLE HANDHELD TISSUE REMOVAL DEVICE

(71) Applicant: GYRUS ACMI, INC., Southborough, MA (US)

(72) Inventor: Joey Magno, Cordova, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 486 days.

(21) Appl. No.: 17/010,026

(22) Filed: Sep. 2, 2020

(65) Prior Publication Data

US 2021/0100574 A1 Apr. 8, 2021

Related U.S. Application Data

(60) Provisional application No. 62/950,591, filed on Dec. 19, 2019, provisional application No. 62/910,676, filed on Oct. 4, 2019.

(51) Int. Cl.
*A61B 17/32* (2006.01)
*A61B 17/00* (2006.01)

(52) U.S. Cl.
CPC ............ *A61B 17/32002* (2013.01); *A61B 2017/00398* (2013.01); *A61B 2017/00477* (2013.01); *A61B 2217/005* (2013.01)

(58) Field of Classification Search
CPC .... A61B 17/32002; A61B 2017/00398; A61B 2017/00477; A61B 2017/0046; A61B 2017/320032; A61B 2217/005
See application file for complete search history.

(56) References Cited

U.S. PATENT DOCUMENTS

| | | | | |
|---|---|---|---|---|
| 2014/0155923 | A1* | 6/2014 | Edwards | ............... A61B 18/14 606/170 |
| 2017/0303990 | A1* | 10/2017 | Benamou | ......... A61B 17/32002 |
| 2019/0110807 | A1* | 4/2019 | Shener-Irmakoglu | ...................... A61B 17/32002 |

* cited by examiner

*Primary Examiner* — Sarah A Long
(74) *Attorney, Agent, or Firm* — Schwegman Lundberg & Woessner, P.A.

(57) ABSTRACT

A tissue removal device, and methods of using the same, are described. An exemplary detachable, handheld tissue removal device comprises a hand piece and a blade assembly removably attachable to the hand piece. The blade assembly includes a rotatable resection member driven to rotate and surgically remove tissue from a target tissue site, and a coupling assembly including a locking member to detachably couple the blade assembly to the hand piece and operatively enable or disable the rotation of the blade assembly relative to the hand piece. The rotation of the blade assembly causes a change in rotating angle of the blade assembly. The coupling assembly can secure the rotating angle of the blade assembly during the tissue resection procedure.

17 Claims, 6 Drawing Sheets

DETACHABLE HANDHELD TISSUE REMOVAL DEVICE

CROSS-REFERENCE TO RELATED APPLICATIONS

This application claims the benefit of priority to U.S. Provisional Patent Application Ser. No. 62/910,676, filed on Oct. 4, 2019 and U.S. Provisional Patent Application Ser. No. 62/950,591, filed on Dec. 19, 2019, the contents of which are incorporated herein in their entireties.

TECHNICAL FIELD

This document relates generally to a tissue removal device, and more specifically relates to a detachable handheld rotating tool for cutting or shaving anatomical structure.

BACKGROUND

Debridement is the medical removal of necrotic, cancerous, damaged, infected or otherwise unwanted tissue. Some medical procedures include, or consist primarily of, the mechanical debridement of issue from a subject. Tissue may be accessed at a remote surgical site, excised from the adjacent anatomy, and the excised tissue removed from the remote surgical site. In certain situations, such as arthroscopic surgery, endoscopic surgery, ENT surgery, etc., relatively small visualization devices and relatively small surgical tools (e.g., graspers, cutters, cauterizers, etc.) are generally introduced into a restricted space within the human body (e.g., the interior of a joint, the interior of the abdomen, the interior of a nasal passage, etc.) and then used at that location for a specific surgical procedure (e.g., to trim meniscal cartilage in a joint, to excise a tissue mass in the abdomen, to excise a tissue mass in a nasal passage, etc.)

One of the tissue removal devices employed in those surgeries is a rotary debrider. The debrider can be motorized to cut and remove tissue from a target site. Because debrider devices with relatively large dimensions risk removing unintended tissue from the subject, or damaging the unintended tissue, debriders with small dimensions and improved cutting precision are desired such that only the desired tissue is resected from the patient, thereby improving patient safety and tissue removal efficiency. Greater flexibility in maneuvering the device is also desired particularly in a procedure performed at a surgical site with restricted space and complex geometry.

OVERVIEW

The present document describes tissue removal devices, and methods of using the same, for resecting and removing unwanted tissue or other material from target locations in a patient body during a minimally invasive or other medical procedure. According to one aspect of the present document, a detachable, handheld tissue removal device comprises a hand piece, and a blade assembly removably attachable to the hand piece. The blade assembly can include a rotatable resection member driven by a motor to rotate and surgically remove tissue from a target tissue site. A coupling assembly, which can be at least partially within the blade assembly, can include a locking member that detachably couples the blade assembly to the hand piece, and operatively enables or disables rotation of the blade assembly relative to the hand piece. The rotation of the blade assembly can cause a change in rotating angle of the blade assembly. The coupling assembly can secure the rotating angle of the blade assembly during the tissue resection procedure.

Example 1 is a medical device for surgically removing tissue, comprising: a hand piece; and a blade assembly removably attachable to the hand piece, the blade assembly including: a rotatable resection member configured to rotate and surgically remove tissue from a target tissue site; and a coupling assembly including a locking member configured to: detachably couple the blade assembly to the hand piece; operatively enable or disable a rotation of the blade assembly relative to the hand piece, the rotation of the blade assembly causing a change in rotating angle of the blade assembly; and secure the rotating angle of the blade assembly.

In Example 2, the subject matter of Example 1 optionally includes the rotatable resection member that can include at least one of: a shaver; a blade; a burr; or a debrider.

In Example 3, the subject matter of any one or more of Examples 1-2 optionally includes the blade assembly that can include an elongate body, comprising: an outer tube; and an inner tube housed within the outer tube and rotatable relative thereto, the inner tube having a resection window to expose the rotatable resection member; wherein the resection window and the rotatable resection member cooperate to shear tissue extending into the resection window.

In Example 4, the subject matter of Example 3 optionally includes the rotatable resection member that can be configured to be driven by a motor to rotatably open and close the resection window to shear tissue extending between a first resection surface of the resection window and a second resection surface of the rotatable resection member.

In Example 5, the subject matter of Example 4 optionally includes the rotatable resection member that can be configured to operate in a oscillation mode to rotate in alternate directions with respect to the resection window.

In Example 6, the subject matter of any one or more of Examples 3-5 optionally includes the coupling assembly that can include: a rotatable first hub coupled to the outer tube of the blade assembly, wherein a rotation of the first hub causes a rotation of the outer tube and a change in rotating angle of the blade assembly relative to the hand piece; and a rotatable second hub coupled to the inner tube of the blade assembly, wherein a rotation of the second hub causes a rotation of the inner tube and a change in an orientation of the resection window with respect to the target tissue site.

In Example 7, the subject matter of Example 6 optionally includes the locking member that can include: a body; at least one graspable tab attached to the body; and an end portion extending from the body, the end portion configured (1) to be operatively received in one of a plurality of locking receptacles to disable the rotation of the outer tube and to secure the blade assembly at the specific rotating angle relative to the hand piece, or (2) to be operatively disengaged from the one of the plurality of locking receptacles to enable the rotation of the outer tube and the change in rotating angle of the blade assembly relative to the hand piece.

In Example 8, the subject matter of Example 7 optionally includes the at least one graspable tab that can be operatively pressed to disengage the end portion from a first locking receptacle, or is operatively released to engage the end portion into a second locking receptacle.

In Example 9, the subject matter of any one or more of Examples 7-8 optionally includes the plurality of locking receptacles that can include recesses circumferentially located on a tubular housing portion of the hand piece.

In Example 10, the subject matter of Example 9 optionally includes the recesses that can be uniformly spaced around an outer circumference of the tubular housing portion of the hand piece.

In Example 11, the subject matter of any one or more of Examples 9-10 optionally includes the plurality of locking receptacles that can include at least five recesses circumferentially located on a tubular housing portion of the hand piece.

In Example 12, the subject matter of any one or more of Examples 6-11 optionally includes the hand piece that can include an actuator adapted to engage and rotate the second hub to change the orientation of the resection window on the inner tube.

In Example 13, the subject matter of Example 12 optionally includes the actuator that can include: a thumbwheel; and a gear assembly including a worm coupled to the thumbwheel via a shaft of the worm, and a worm wheel meshing with the worm and engaging the second hub; wherein a rotation of the thumbwheel causes a change in the orientation of the resection window via the gear assembly, the second hub, and the inner tube.

In Example 14, the subject matter of Example 13 optionally includes the gear assembly that can be configured to: transmit a forward rotation of the thumbwheel towards a distal end of the blade assembly into a first direction of rotation of the resection window; and transmit a backward rotation of the thumbwheel towards a proximal end of the blade assembly into a second direction, opposite the first direction, of rotation of the resection window.

In Example 15, the subject matter of any one or more of Examples 13-14 optionally includes the actuator that can include two thumbwheels laterally disposed on opposite sides of a tubular housing portion of the hand piece, the two thumbwheels coupled to the gear assembly at opposite terminals of the worm shaft.

In Example 16, the subject matter of any one or more of Examples 1-15 optionally includes the hand piece that can include first one or more ports open to a lumen of the inner tube or an annular space between the inner tube and the outer tube, the first one or more ports configured to receive irrigation fluid to irrigate the rotatable resection member.

In Example 17, the subject matter of any one or more of Examples 1-16 optionally includes the hand piece that can include second one or more ports open to a lumen of the inner tube, the second one or more ports operatively coupled to a vacuum source configured to apply suction pressure to withdraw the resected tissue from the target tissue site.

Example 18 is a method of operating a detachable handheld medical device to surgically remove tissue from a target tissue site. The method comprises steps of: connecting a removable blade assembly to a hand piece; rotating the blade assembly to a specific rotating angle with respect to the hand piece; securing the blade assembly at the specific rotating angle via a coupling assembly; adjusting an orientation of a resection member associated with the blade assembly with respect to the target tissue site via an actuator on the hand piece; and resecting and removing tissue from the target site using the resection member.

In Example 19, the subject matter of Example 18 optionally includes unlocking the coupling assembly from the hand piece; and disconnecting the blade assembly from the hand piece.

In Example 20, the subject matter of any one or more of Examples 18-19 optionally includes resecting and removing tissue that can include driving a rotation of the rotatable resection member relative to a resection window on a rotatable inner tube disposed within the blade assembly, the resection member rotatably opening and closing the resection window to shear tissue extending into the resection window.

In Example 21, the subject matter of Example 20 optionally includes driving a rotation of the rotatable resection member that can include alternating between first and second rotating directions of the rotatable resection member relative to a resection window.

In Example 22, the subject matter of any one or more of Examples 19-21 optionally includes securing the blade assembly at the specific rotating angle that can include engaging an end portion of a locking member into one of a plurality of locking receptacles circumferentially located on a tubular housing portion of the hand piece, wherein the engagement of the end portion of the locking member prevents the blade assembly from rotating with respect to the hand piece and secure the specific rotating angle of the blade assembly.

In Example 23, the subject matter of Example 22 optionally includes unlocking the coupling assembly from the hand piece that can include disengaging the end portion of the locking member from the one of the plurality of locking receptacles, wherein the disengagement of the end portion of the locking member enables the blade assembly to rotate with respect to the hand piece to change the rotating angle.

In Example 24, the subject matter of Example 23 optionally includes, securing the blade assembly by pressing the end portion of a locking member to disengage the end portion from a first locking receptacle; and unlocking the coupling assembly by releasing the end portion of a locking member to engage the end portion into a second locking receptacle.

In Example 25, the subject matter of any one or more of Examples 18-24 optionally includes adjusting the orientation of a resection member that can include rotating a resection window opened on a rotatable inner tube disposed within the blade assembly.

In Example 26, the subject matter of Example 25 optionally includes adjusting the orientation of a resection window by rotating a thumbwheel in one of two opposite directions, the thumbwheel disposed on a lateral side on a tubular housing portion of the hand piece, the rotation of the thumbwheel transmitted via a gear assembly into a rotation of the rotatable inner tube and the rotation of resection window thereon.

In Example 27, the subject matter of Example 26 optionally includes rotating the thumbwheel that can include rotating the thumbwheel in a forward rotation towards a distal end of the blade assembly to cause a first direction of rotation of the resection window, or rotating the thumbwheel in a backward rotation towards a proximal end of the blade assembly to cause a second direction, opposite the first direction, of rotation of the resection window.

In Example 28, the subject matter of any one or more of Examples 18-27 optionally includes injecting irrigation fluid via one or more first ports on the hand piece to irrigate the rotatable resection member during tissue resection and removal.

In Example 29, the subject matter of any one or more of Examples 18-28 optionally includes applying suction pressure via one or more second ports on the hand piece to withdraw the resected tissue from the target tissue site.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Tissue removal devices, such as powered debriders, are needed which can be produced with sufficient mechanical complexity and a small size so that they can both safely and more efficiently remove tissue from a subject, and/or remove tissue in a less invasive procedure and/or with less damage to adjacent tissue such that risks are lowered and recovery time is improved. Conventional tissue removal devices in the art tend to suffer from several disadvantages. By way of example and not limitation, some conventional tissue removal devices have limited flexibility to access a remote surgical site with restricted space and complex geometry. For example, for some tissue removal devices, the workpiece (e.g., one or more resection members) can only be set and retained at one of a few (e.g., two to four) positions during the procedure. Such a lack of versatility can be a challenge for an operator (e.g., a surgeon) to quickly and accurately position and/or orient the resection member to an optimal surgical site with respect to the target tissue to be removed, while maximally avoid damaging unintended tissue from the subject. Additionally, some conventional tissue removal devices lack the flexibility of tuning motions of the resection member, such as fine adjustment of the facing of the resection member during the tissue removal procedure.

Some tissue removal devices include disposable parts. For example, a disposable blade assembly (including the resection member) can be removed from the device body, and a replacement blade assembly can be connected to the device body. Such reconfigurable structures provide a cost-saving benefit. However, for many current tissue removal devices, the configuration process can be inefficient, time-consuming, and complicated. Moreover, the disposable blade assemblies in the art often include additional components besides the resection member, such as parts for transferring an operator's motion of maneuvering the device into the rotation of the resection member. This can increase the complexity and cost of the disposable blade assembly. For at least the foregoing reasons, the present inventors have recognized an unmet need for a new tissue removal device that can improve upon the deficiencies of the prior art.

Disclosed herein are tissue removal devices, and methods of the same, for resecting and removing unwanted tissue or other material from target locations within a body of a patient during a minimally invasive or other medical procedure. The devices and methods described herein improve upon the deficiencies of tissue removal devices of the prior art. Among other things, the tissue removal devices according to various embodiments discussed in this document can advantageously provide more flexibility in controlling and maneuvering the device (e.g., position and orientation of the blade assembly and the resection member). The tissue removal devices have unique designs of actuators adapted for operators with different gripping styles or handedness, which can enhance operation reliability and user experience. The detachable configuration, in accordance with various examples of the coupling assembly as discussed in this document, can provide greater ease of maintenance of the device, increased portability and versatility, and reduce the complexity and overall cost of the disposable blade assembly.

Figure 1:
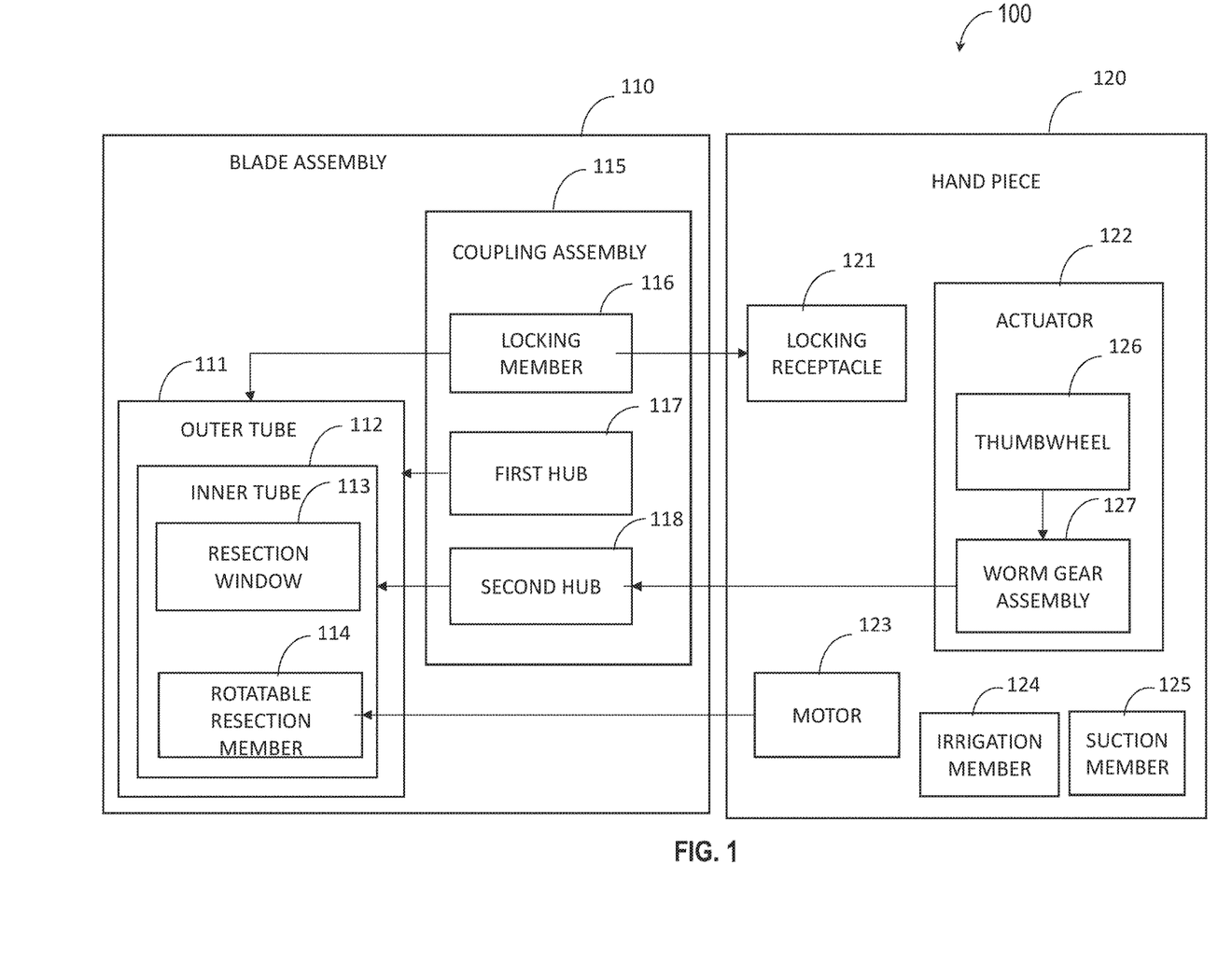
FIG. 1 is a block diagram illustrating exemplary configuration and components of a handheld tissue removal device for rotationally resecting and removing target anatomical structures in a patient body.

FIG. 1 is a block diagram illustrating, by way of example and not limitation, configuration and components of a handheld tissue removal device 100 for rotationally resecting and removing target anatomical structures in a patient body. The tissue removal device 100 can include a blade assembly 110 and a hand piece 120. The blade assembly 110 can include a rotatable resection member that, controlled by one or more control elements in the hand piece 120, can be driven to rotate and surgically remove tissue. In this document, "resecting" or "resection" can include various excision modes such as, by way of non-limiting example, cutting, clipping, shearing, shaving, deburring, grinding unwanted tissue or other material from a target cite in a patient body. The tissue excision modes can be achieved by using different types of resection members. The blade assembly 110 can be detachably coupled to the hand piece 120, as to be described in accordance with various examples presented in this document.

The blade assembly 110 can be removably attachable to the hand piece 120. The blade assembly 110 can be at least partially disposable. In an example, the blade assembly 110 has a modular design, and can include an elongate body that houses one or more resection remembers, and a coupling assembly 115. The elongate body can include an outer tube 111, and an inner tube 112 disposed within the outer tube 111. A rotatable resection member 114 can be coaxially mounted at least partially within the inner tube 112, and driven to rotate axially therein. Examples of the rotatable resection member 114 may include a shaver, a blade, a burr, or a debrider, among other tissue resection structures. The rotatable resection member can provide respective modes of tissue resection.

The rotatable resection member 114 can be exposed through a resection window 113 on the inner tube 112, such as a distal portion of the inner tube 112. In accordance with various examples, the resection window 113 and the rotatable resection member 114 can have respective resection surfaces. The rotatable resection member 114 can sweep across the resection window 113 (which stays stationary relative to the rotating resection member 114), repeatedly open and close the resection window 113, whereby to shear off tissue extending into the resection window 113 and into an interior of the inner tube 112, such as under suction pressure. In an example, the rotatable resection member 114 can alternate between a first rotation direction (e.g., clockwise rotation) and a second rotation direction (e.g., counter-clockwise rotation) with respect to the resection window 113, a resection mode hereinafter referred to as an oscillation mode. The resection window 113 (or the inner tube 112 as a whole) may hereinafter referred to as an "outer blade", and the rotatable resection member 114 referred to as an "inner blade". Examples of the blade assembly 110, including the outer and inner tubes in the elongate member, are described below such as with reference to FIG. 2.

The coupling assembly 115 can detachably couple the blade assembly 110 to the hand piece 120. The coupling assembly 115 can include a locking member 116 affixed to the outer tube 111. In some examples, the locking member 116 can be included in the hand piece 120. The locking member 116 can be adapted to engage into, or disengage from, a locking receptacle 121 on the hand piece 120. Engagement of the locking member 116 into the locking receptacle can help secure the coupling between the blade assembly 110 and the hand piece 120. Disengagement of the locking member 116 can help decouple the blade assembly 110 from the hand piece 120. When the locking member 116 is disengaged from the locking receptacle 121, a user can manually rotate the elongate member of the blade assembly 110 to change a rotating angle of the blade assembly 110 relative to the hand piece 120, such as to position the resection window 113 at a desired surgical site proximate the target tissue to be removed. After positioning and/or orienting the elongate member at the desired rotating angle, the locking member 116 can be engaged into the locking receptacle 121. This effectually keeps the elongate member of the blade assembly 110 from rotating freely about the hand piece 120. As such, the desired rotating angle of the blade assembly 110 can be "locked" during the tissue removal procedure. Examples of the locking member 116 and the locking receptacle 121 are described below, such as with reference to FIGS. 3, 4A-4B, and 5A-5B.

The coupling assembly 115 can include a first rotatable hub 117 and a second rotatable hub 118. The first hub 117 can be non-rotationally affixed to the outer tube 111, such that rotation of the first hub 117 can cause non-slip rotation of the outer tube 111. In an example, when the locking member 116 is in an "unlocked" position (e.g., disengaged from the locking receptacle 121), an operator may manually turn the first hub 117 or the outer tube 111, thereby changing the rotating angle of the elongate member of the blade assembly 110 to position the outer blade (the resection window 113) and the inner blade (the rotatable resection member 114) at a desired surgical site.

The second hub 118 can be coupled to the inner tube 112 of the blade assembly 110. As illustrated herein, the second hub 118 can be rotated via an actuator 122 in the hand piece 120. The rotation of the second hub 118 causes rotation of the inner tube 112, thereby changing the orientation (or the facing) of the resection window 113 on the inner tube 112. Examples of the second hub 118 and change of the resection window orientation are discussed below with reference to FIGS. 3 and 5A-5B.

The hand piece 120 can include a locking receptacle 121, an actuator 122, and a motor unit 123. The locking receptacle 121 can be configured to receive a latching portion of the locking member 116, such that the blade assembly 110 is engaged with the hand piece 120. The actuator 122 can include at least one manually turntable thumbwheel 126, and a worm-gear assembly 127 that couples the thumbwheel 126 to the second hub 118. An operator can turn the thumbwheel 126, and the worm-gear assembly 127 can transmit the turning motion of the thumbwheel 126 into rotation of the second hub 118, and further an axial rotation of the inner tube 113, which would cause a change in the orientation (or facing) of the resection window 113. In an example, the thumbwheel 126 can be turned in both directions (e.g., clockwise and counter-clockwise, or forward and backward directions). The inner tube 112 and the resection window 113 can rotate in both directions accordingly. By changing the rotating angle of the elongate member of the blade assembly 110 (also referred to as a "big motion") via the first hub 117 or the outer tube 111, and further changing the orientation (or the facing) of the resection window 113 (also referred to as a "fine motion") via the second hub 118 and the inner tube 112, the resection members can be controlled with increased flexibility and precision, particularly at a surgical site with restricted space and complex geometry.

The motor 123 can drive the rotation of the rotatable resection member 114 relative to the resection window 113, such as via a drive train coaxially mounted within a central lumen of the inner tube 112. Examples of the motor 123 can include a stepper motor, or other types of electric, pneumatic or hydraulic motors, servos, or other prime movers. The rotatable resection member 114 and the resection window 113 can have respective resection surfaces. The rotatable resection member 114 can repetitively sweep across the resection window 113 in an oscillation mode, and shear off tissue extending into the resection window 113 such as under suction pressure. In an example, under the oscillation mode, the rotatable resection member 114 can alternate between a first rotation direction (e.g., clockwise rotation) and a second rotation direction (e.g., counter-clockwise rotation), with approximately 6-8 rotations in each direction.

The hand piece 120 can include an irrigation member 124, including one or more ports open to the central lumen of the inner tube 112. An irrigation source can inject irrigation fluid via the irrigation ports into an irrigation conduit leading to an opening of the inner tube 112. Alternatively, the irrigation fluid can travel through an annular space between the inner tube 112 and the outer tube 111. The irrigation fluid can serve one or more functions including, by way of example and not limitation, lubricating the resection members (e.g., outer and inner blades) and various coupling members and rotating members, cooling the resection elements and the tissue being cut, absorbing heat and carrying it away as the irrigation fluid is withdrawn from the surgical site, flushing tissue particles from the moving parts to prevent them from becoming clogged around the target tissue, and carrying away the tissue portions being cut and removing them from the surgical site, etc.

In some examples, the hand piece 120 can include a suction member 125, such as one or more suction ports open to a passage leading to the interior of the inner tube 112. The suction ports can be coupled by a tissue suction conduit to a vacuum source, or other aspiration device, for applying suction pressure to the interior of the inner tube 112 to withdraw the excised tissue through the interior of the inner tube 112. In an example, seals can be plugged into the suction ports to prevent leakage of irrigation fluid during irrigation. The seals can be removed or otherwise made conduct in response to the suction pressure applied by the vacuum source. In some examples, the suction member 125 can additionally or alternatively include valves controllably gate flow of resected tissue.

Figure 2:
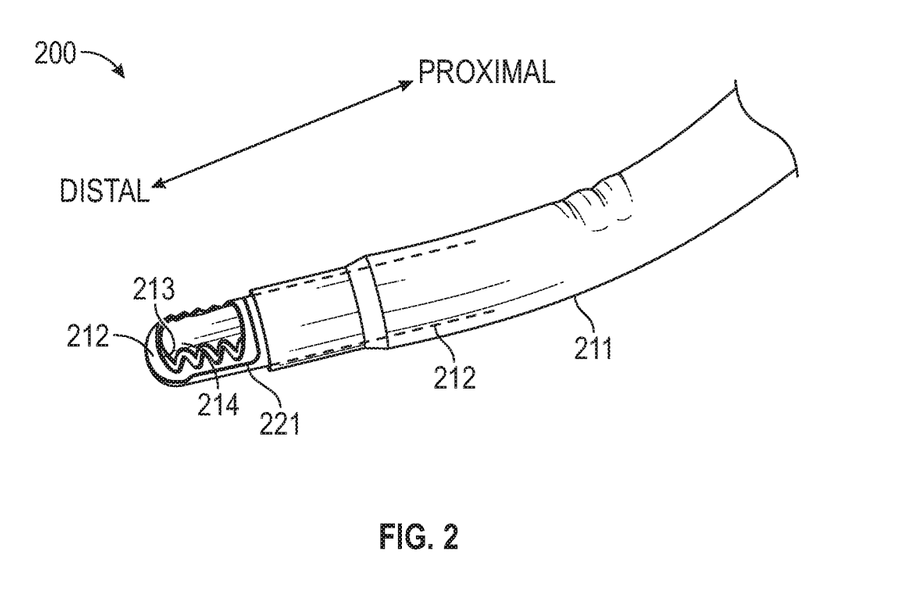
FIG. 2 illustrates a perspective view of at least a portion of an exemplary blade assembly in a handheld tissue removal device.

FIG. 2 illustrates a perspective view of at least a portion of an exemplary blade assembly 200 in a handheld tissue removal device, which is an example of the blade assembly 110 of the resection device 100. The blade assembly 200 can include a cylindrical body comprising an outer tube 211 (which is an example of the outer tube 111), and an inner tube 212 (which is an example of the inner tube 112) coaxially aligned within an interior of the outer tube 211 and configured to rotate axially relative thereto. At a distal portion of the blade assembly body, the outer tube 211 has an opening 221 sizable to allow a distal portion of the inner tube 212 to extend therefrom. At its distal portion, the inner tube 212 can enclose and engage a rotatable resection member 214 (which is an example of the rotatable resection member 114). In some examples, the rotatable resection member 214, and the power train coupling the motor 123 to the rotatable resection member 214, can be housed in a third tube coaxially mounted within a central lumen of the inner tube 112.

A resection window 213 (which is an example of the resection window 113) can open on a circumferential surface proximate the distal portion of the inner tube 212. The resection window 213 can be sized, shaped, or otherwise configured to expose at least a portion of the rotatable resection member 214. The resection window 213 and the rotatable resection member 214 can have respective resection surfaces, such as serrations, knife edges, toothed cutting blades, shearing blades, among other suitable cutting surfaces. The rotatable resection member 214, when driven by a motive source such as the motor 123, can rotate axially within the interior of the inner tube 212, while the inner tube remains relatively stationary. The rotatable resection member 214 and the resection window 213 can cooperate to provide repetitive scissoring actions to excise tissue extending into the resection window 213 between the respective resection surfaces of the resection window 213 and the rotatable resection member 214. The resected tissue can be withdrawn from the surgical site, such as under the suction pressure applied to the resection window 213 and the inner tube 212 by an external vacuum source.

Figure 3:
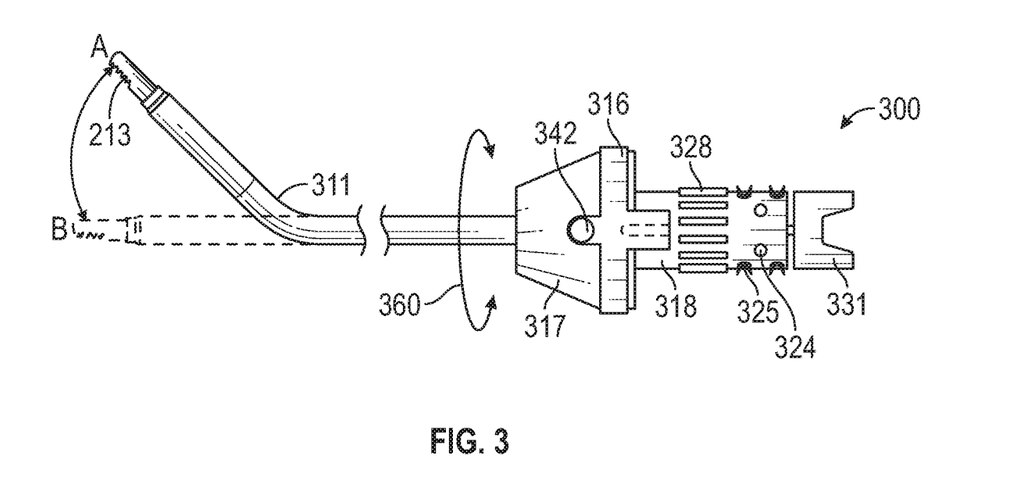
FIG. 3 illustrates a side view of at least a portion of an exemplary coupling assembly in a handheld tissue removal device, and a portion of a hand piece coupled to a blade assembly.

FIG. 3 is a diagram illustrating a side view of at least a portion of a coupling assembly 300 in a handheld tissue removal device, and a portion of a hand piece coupled to a blade assembly. The coupling assembly 300, which is an example of the coupling assembly 115 of the resection device 100, can include, among other elements, a nose hub 317, a rotating hub 318, a release button 342, and a locking member 316. The cone-shaped nose hub 317, which is an example of the first hub 117, can be rigidly fixed to an outer tube of an elongate member 311 of a rotating blade assembly. The elongate member 311 is an example of the cylindrical body of the blade assembly 200, and can house an outer tube, an inner tube (the "outer blade"), and a motorized rotatable resection member (the "inner blade"). An operator can hold and turn the nose hub 317 in one of two directions 360 as shown in FIG. 3. The rotation of the nose hub 317 causes a change in rotating angle of the elongate member 311 relative to the hand piece, such as from a first position "A" to a different second position "B", as shown in FIG. 3. The position and orientation of resection window 213 can be changed accordingly. When a desired surgical site is reached, the locking member 316, which is an example of the locking member 116, can be engaged to the locking receptacles on the hand piece, thereby keeping the elongate member 311 from free rotation about the hand piece. The desired rotating angle of the elongate member can be locked during the tissue removal procedure. Examples of the locking member are described below, such as with reference to FIGS. 4A-4B and 5.

The blade assembly can be disconnected from the hand piece for maintenance (e.g., cleaning, sterilization, or repair) or for replacement. In an example, the elongate member 311, and at least a portion of the coupling assembly 300 (e.g., the nose hub 317, and optionally the rotating hub 318), are disposable. A replacement blade assembly can be connected back to the hand piece. The detachable engagement can be achieved using the release button 342 to activate engagement or disengagement. Examples of the engagement include a snap-fit coupling, a threaded or other rotation or screw-in coupling, a slide-in engagement, or one or more other locking mechanisms. In an example, the release button 342 can be coupled to the locking member to activate detachable engagement between the blade assembly and the hand piece, examples of which are described below with reference to FIGS. 4A-4B and 5.

The rotating hub 318, which is an example of the second hub 118 of the resection device 100, can be coupled to the inner tube of the blade assembly 311. The rotating hub 318 can also be coupled to an actuator in a hand piece. FIG. 3 illustrates a portion of the actuator, including a worm wheel 328, which can be a part of the gear assembly 127. As illustrated in FIG. 3, the rotating hub 318 is coupled to the axel shaft of the worm wheel 328. By turning the thumbwheel, the worm gear assembly can transmit the turning motion to rotation of the rotating hub 318 and the inner tube, and a rotation of resection window 213, in a range of 0-360 degrees or a specific range therebetween. Examples of the thumbwheel and the worm gear assembly are described below, such as with reference to FIGS. 4A-4B and 6A-6B.

The hand piece coupled to a blade assembly 300 may also include a power transmission component 331 coupled to a motive source, such as the motor 123, that drives the rotation of the rotatable resection member 114 within the elongate member 311. The hand piece can include one or more irrigation ports 324 (which are examples of the irrigation member 124) for receiving irrigation fluid to irrigate the outer and inner blades and the surrounding tissue during a resection operation, and/or one or more sealable suction ports 325 (which are examples of the suction member 125) to receive suction pressure produced by a vacuum source to withdraw the resected tissue, as described above with reference to FIG. 1.

Figures 4A, 4B:
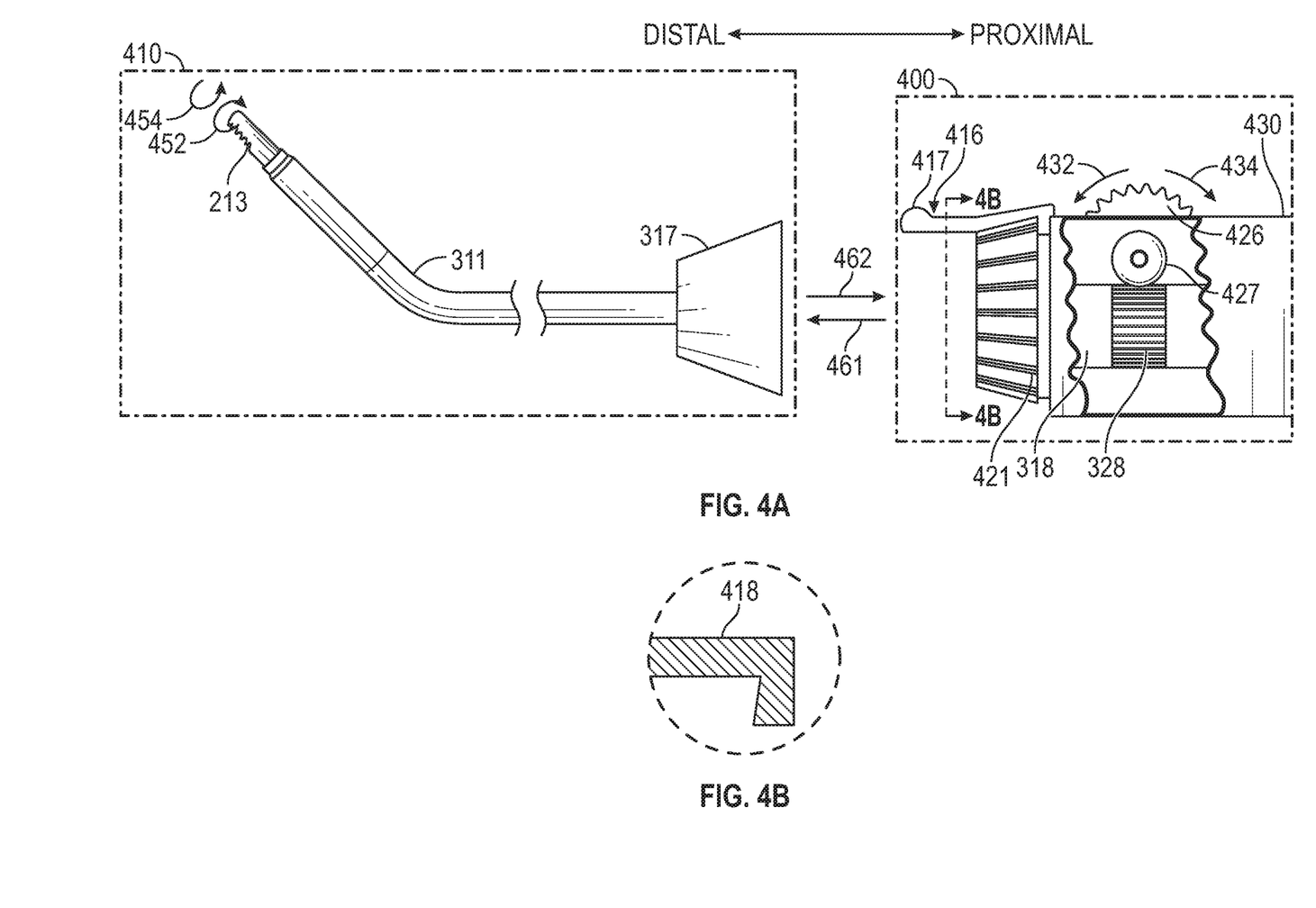
FIG. 4A illustrates a side sectional view of at least portion of an exemplary hand piece in a handheld tissue removal device.
FIG. 4B illustrates a front view of an end portion of an exemplary coupling assembly.

FIG. 4A illustrates a side sectional view of at least a portion of a hand piece 400 in a handheld tissue removal device, with a side portion of the housing of the hand piece removed. Also shown in FIG. 4A is a portion of the coupling assembly removably engageable with the hand piece 400. The hand piece 400, which is an example of the hand piece 120, can include a thumbwheel 426 coupled to a shaft of a worm 427. The thumbwheel 426 can be located in parallel to a tubular housing portion 430 of the hand piece. The thumbwheel 426 can rotate in both directions, such as a clockwise or a counter-clockwise, or a "forward" direction 432 toward the distal end of the blade assembly 410, or a "backward" direction 434 toward the proximal end of the blade assembly.

The worm 427 can mesh with the worm wheel 328 to form a worm-gear assembly that, as an example of the worm-gear assembly 127, can alter the direction of the rotational motion of the thumbwheel 426. For example, the gear assembly can transmit the forward rotation 432 of the thumbwheel 426 into a first direction 452 of rotation of the resection window 213, or transmit the backward rotation 434 of the thumbwheel into a second direction 454, opposite the first direction, of rotation of the resection window 213.

The worm-gear assembly can also transfer the thumbwheel rotational motion into a rotational motion of the worm wheel 328 and the rotating hub 318 coupled thereto with an altered speed. For example, by choosing a worm wheel 328 with a specific number of teeth, a desired gear ratio of the worm-gear assembly and a desired speed reduction can be achieved. An operator can use the thumbwheel 426 to fine-tune the orientation of the resection window 213 with high precision and improved efficiency.

The worm-gear assembly can include other types of gear arrangement to transfer rotation of the thumbwheel 426 to rotation of the rotating hub 318, thereby changing the orientation of the resection window 213. In an example, the worm-gear assembly may include a gear set of one or more intermediate gears coupled between the worm 427 and the worm wheel 328.

The hand piece 400 can include a plurality of locking receptacles 421 configured to receive a portion of a locking latch 416. The locking latch 416, which is an example of the locking member 116 or the locking member 316, can include at least one graspable tab portion 417, and an end portion 418. FIG. 4B illustrates a front view of the end portion 418 of the coupling assembly along the "4B-4B" direction as shown in FIG. 4A. The tab portion 417 can be an example of the release button 342, and can be pressed to disengage the end portion 418 from the locking receptacles 421. The blade assembly 410, including the nose hub 317 and the attached elongate member 311, can then be disconnected from the hand piece 400 (as indicated by arrow 461). A cleaned, sterilized, or repaired blade assembly, or a replacement blade assembly, can be connected to the hand piece 400 (as indicated by arrow 462), such as via respective couplers on the nose hub 317 of the hand piece 400, and on the blade assembly 410. An operator may manually rotate the nose hub 317 to change the rotating angle of the elongate member 311 relative to the hand piece 400, such that the resection window 213 is positioned and oriented in a surgical site proximate the target tissue to be removed.

When the elongate member of the blade assembly 110 is positioned and/or oriented to a desired rotating angle, the locking member 116 can be engaged into the locking receptacle 121, the tab 417 can be released, such that the end portion 418 can reengage into one of the locking receptacles 421, and the new blade assembly is securely connected to the hand piece. In addition to connection or disconnection between the blade assembly 410 and the hand piece 400, engaging the end portion 418 into a locking receptacle can also prevent the elongate member 311 from rotating. The rotating angle of the elongate member 311 relative to the hand piece 400 can be retained with enhanced stability during the tissue removal process.

The plurality of locking receptacles 421 can take the form of a plurality of recesses circumferentially located on an outer surface of the hand piece. The locking latch 416 may function as a hinge or a lever to effect motion toward or away from the recesses on the outer surface of the hand piece. In an example, the recesses can include 5-20 grooves sized and shaped to securely receive and retain a portion of the locking latch 416. The grooves can be uniformly spaced around an outer circumference of the tubular housing portion 430 of the hand piece. With multiple receptacles or grooves on the hand piece, the locking mechanism discussed herein (including the locking latch 416 and the locking receptacles 421) increases flexibility of resection member position control, and improve upon the deficiencies of prior art tissue removal devices which often have a limited positions or orientations for locking the resection blade.

Figure 5A:
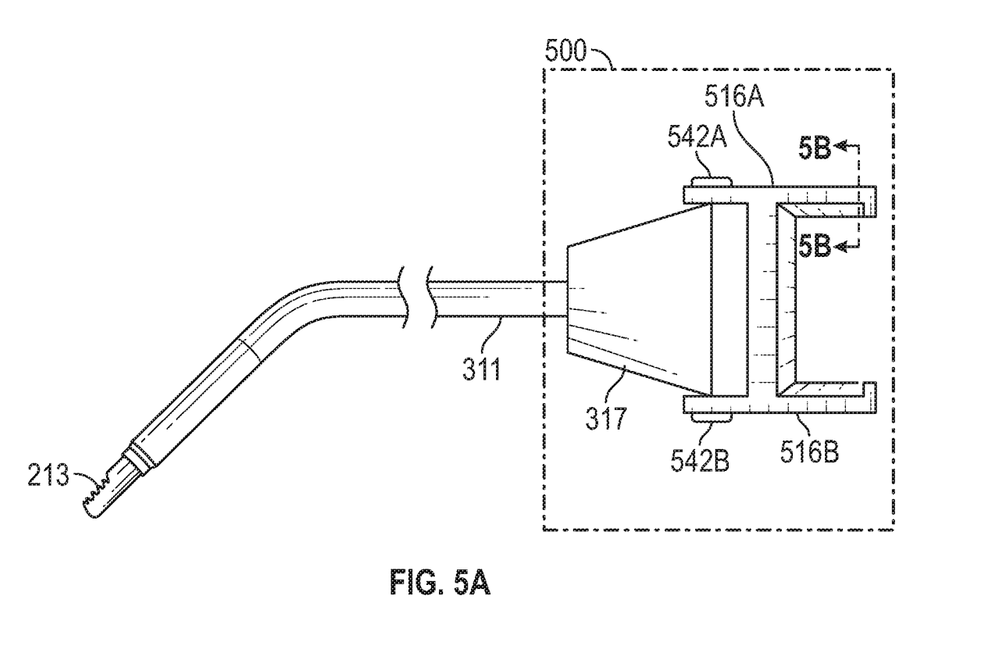
FIG. 5A illustrates a top view of at least a portion of an exemplary coupling assembly in a handheld tissue removal device.
Figure 5B:
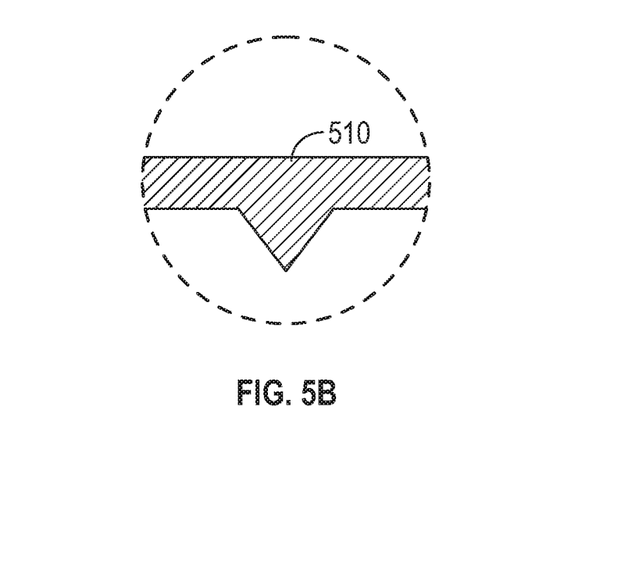
FIG. 5B illustrates a side view of a tab portion of a locking member of the coupling assembly as shown in FIG. 5A.

FIG. 5A illustrates a top view of at least a portion of an exemplary coupling assembly 500 in a handheld tissue removal device. The coupling assembly 500, which is an example of the coupling assembly 115 or the coupling assembly 300, can include a nose hub 317 configured to be non-rotatable fixed to an outer tube of an elongate member 311, and locking members 516A-516B detachably coupled to the nose hub 317. In an example, the locking members 516A-516B, which are examples of the locking member 310 shown in FIG. 3, can be coupled to respective release buttons 542A-542B, which are examples of the release button 342 (e.g., side views of the release button 342). In the example illustrated in FIG. 5, the release button 542A and the corresponding locking member 516A are located at one side of a circumferential exterior surface of the nose hub 317, and the release button 542B and the corresponding locking member 516B are located at the opposite side of the circumferential exterior surface of the nose hub 317. In an example, the locking members 516A-516B may each take the form of a locking latch, such as the locking latch 416 as illustrated in FIG. 4. The locking latches can be configured to engage into respective locking receptacles (e.g., among the locking receptacles 421). FIG. 5B illustrates a side view of a tab portion 510 of a locking latch (an example of the locking member 542A) along the "5B-5B" direction as shown in FIG. 5A. An operator may use the release buttons 542A-542B to engage the locking members 516A-516B. For example, by pressing said release buttons, the locking members 516A-516B can be disengaged from the respective locking receptacles, and the blade assembly can be disconnected from the hand piece. A replacement blade assembly, or a cleaned or repaired blade assembly, can be connected to the hand piece, when the release buttons 542A-542B engage the nose hub 317 of the blade assembly. When the elongate member 311 is positioned in a desired rotating angle, the locking members 516A-516B can be reengaged into respective locking receptacles to lock and stably retain the rotating angle of the elongate member 311 relative to the hand piece.

Figure 6A:
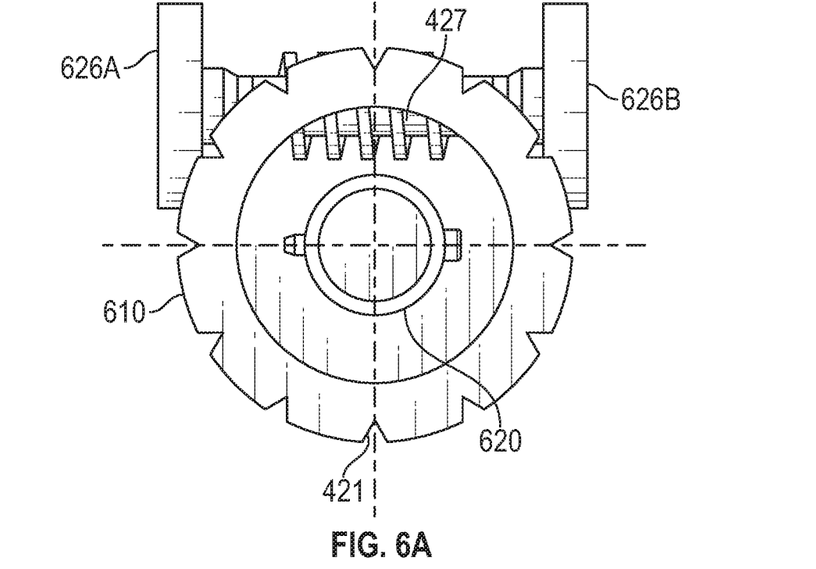
FIG. 6A illustrates a side view of a tubular portion of the hand piece as shown in FIG. 4A.

FIG. 6A illustrates a side sectional view, along the "4B-4B" direction as shown in FIG. 4A, of a tubular housing portion 610 of the hand piece 400. A plurality of locking receptacles 421 can be spaced around an outer circumference of the tubular housing portion 610. As described above with reference to FIG. 4A, the locking receptacles 421 can take the form of recesses, or grooves, configured to receive a portion of a locking member, such as an end portion of the locking latch 416. A coupler 620, co-axially disposed inside the tubular housing portion 610, can be configured to couple the blade assembly to the hand piece.

Figure 6B:
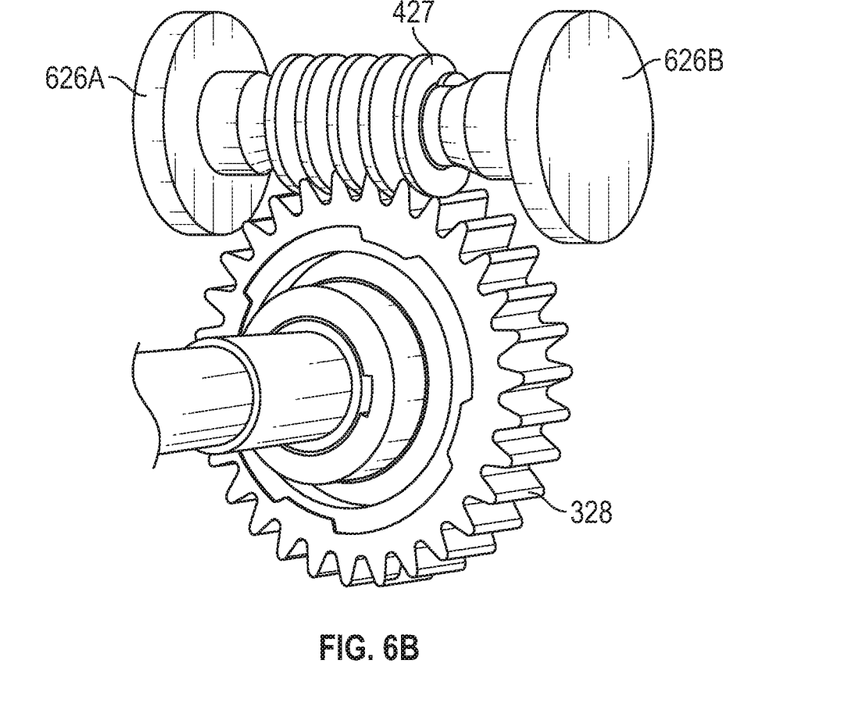
FIG. 6B illustrates a perspective view of a worm-gear assembly in a hand piece in a handheld tissue removal device.

Also shown in FIG. 6A are two thumbwheels 626A-626B laterally disposed on opposite sides of the tubular housing portion 610 of the hand piece. The thumbwheels 626A-626B, which are examples of the thumbwheel 126 or the thumbwheel 426, can be coupled to the worm gear assembly. By way of example, FIG. 6B illustrates a perspective view of the worm-gear assembly 127, comprising a worm 427 meshing with the worm wheel 328. The thumbwheels 626A-626B are coupled to the worm 427 at opposite terminals of the worm shaft. Similar to the description above with reference to FIG. 4A, by rotating either of the thumbwheels 626A-626B, an operator can precisely and effectively fine-tune the orientation of the resection window 213 of the outer blade in a range of 0-360 degrees with improved efficiency and high precision, via the worm-gear assembly, the second hub 318, and the inner tube of the blade assembly.

The two thumbwheels 626A-626B on opposite sides of the tubular housing portion 610 of the hand piece can be advantageous over a single actuator in some conventional tissue removal devices. For example, the two thumbwheels 626A-626B can be adapted to the handedness of the operator. In an example, a left-handed operator may choose to operate the thumbwheel 626A, and a right-handed operator may find it easier to operate the thumbwheel 626B. In both cases, same direction of motion of the thumbwheel can lead to the same direction of rotation of the resection window 213 on the elongate member of the blade assembly. The thumbwheels 626A-626B, among other features as described herein, improves the flexibility of positioning and orienting the blade assembly and adjusting the facing of the resection member, enhances user experience, and increases the efficiency of tissue removal procedure.

Figure 7:
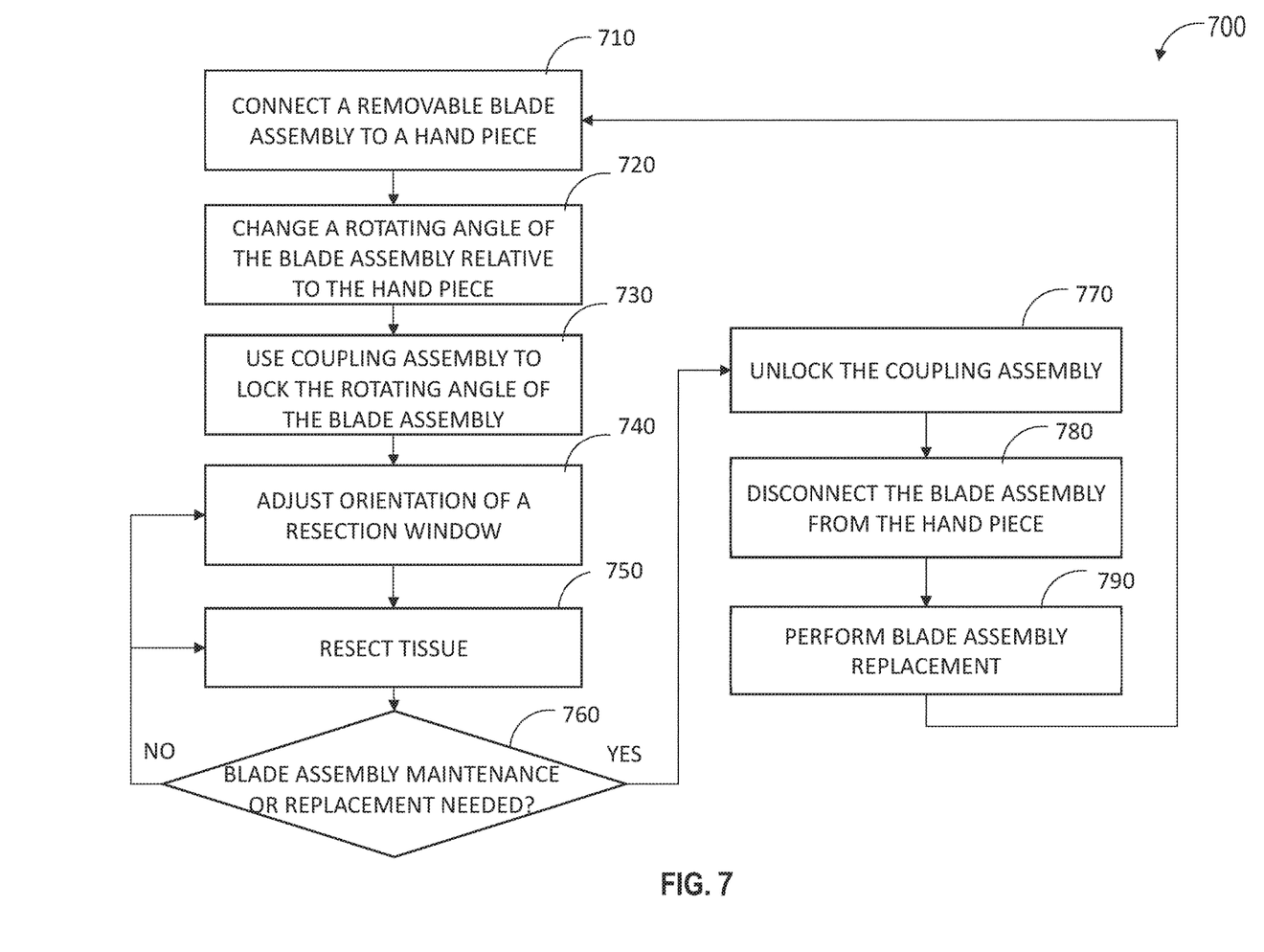
FIG. 7 is a flow chart illustrating an exemplary method of operating a handheld tissue removal device for rotationally resecting and removing target tissue in a patient body.

FIG. 7 is a flow chart illustrating a method 700 of operating a handheld tissue removal device for rotationally resecting and removing target tissue in a patient body. By way of example and not limitation, the handheld tissue removal device can be made and configured in accordance with the block diagram of the detachable, handheld tissue removal device 100 as shown in FIG. 1. The handheld tissue removal device can include a blade assembly (e.g., the blade assembly 200 as shown in FIG. 2), and a hand piece (e.g., the hand piece 400 as shown in FIG. 4A). The hand piece can be removably attachable to the blade assembly via a coupling assembly, such as the coupling assembly 300 as shown in FIG. 3.

The method 700 comprises one or more processes of attaching the blade assembly to the hand piece, positioning and/or orienting the blade assembly to a desired surgical site, resecting and removing tissue, and disconnecting the blade assembly from the hand piece for maintenance or replacement. Although these processes are drawn in one flow chart, they are not necessarily performed in a particular order as shown. In various examples, some of the processes can be performed in a different order.

At 710, the removable blade assembly can be connected to the hand piece, such as via respective couplers on the nose hub 317 of the hand piece 400, and on the blade assembly 410, as indicated by an arrow 462 in FIG. 4. The connected blade assembly can rotate axially with respect to the hand piece. At 720, an operator may manually rotate the nose hub 317 to change the rotating angle of the elongate member 311 of the blade assembly 410 relative to the hand piece 400, such as from a first position "A" to a different second position "B" as shown in FIG. 3. The adjustment of the blade assembly (also referred to as the "big motion") can be performed until the resection members on the blade assembly (e.g., the resection window 213, also referred to as the "outer blade", on an inner tube of the blade assembly) is in a desired position and orientation, such as reaching a surgical site in close proximity to the target tissue to be removed.

At 730, the desired rotating angle of the blade assembly can be locked during the tissue removal procedure using the coupling assembly. The locking can be achieved by engaging a locking member (such as a locking latch 416 or 516) of the coupling assembly into one of a plurality of locking receptacles. The locking member may function as a hinge or a lever to effect motion toward or away from the locking receptacle on the outer surface of the hand piece. In an example as discussed with reference to FIG. 4, the tab of the locking member can be released, such that the end portion of the locking member can engage into a locking receptacle on the outer surface of the hand piece. The engagement between the locking member and the locking receptacle can not only secure the connection between the blade assembly and the hand piece, but can also keep the elongate member of the hand piece from rotating during the tissue removal procedure, thereby stabilizing the desired rotating angle of the blade assembly during the tissue resection procedure. The locking receptacles can include recesses or grooves sized and shaped to securely receive and retain a portion of the locking member. The recesses or grooves can be uniformly spaced around an outer circumference of a tubular portion of the hand piece. In an example, the locking receptacles can include 5-20 recesses or grooves. With a large number of receptacles or grooves on the hand piece, the locking mechanism discussed herein can improve upon the deficiencies of prior art tissue removal devices, which often have a limited positions or orientations for locking the resection blade.

At 740, an orientation of a resection member, such as the resection window (the "outer blade") on the elongate member of the blade assembly, can be adjusted. Rotation of the inner tube and the resection window thereon can be controlled by an actuator on the hand piece, which can include at least one manually turnable thumbwheel and a worm-gear assembly couple the thumbwheel to the inner tube. A manual rotation of the thumbwheel 126 can be transmitted by the worm-gear assembly 127 into an axial rotation of the inner tube, thus changing the facing or orientation of the resection window. By choosing a worm wheel 328 with a specific number of teeth, desired gear ratio and speed reduction can be achieved, which allows for fine-tuning of orientation of the resection window in a range of 0-360 degrees with improved efficiency and high precision.

The thumbwheel can be turned in both directions (e.g., clockwise and counter-clockwise, or forward and backward), causing the inner tube and the resection window to rotate in both directions, as illustrated in FIG. 4A. In some examples, two thumbwheels can be laterally disposed on opposite sides of the tubular housing portion of the hand piece. This can improve the ease of use and enhance user experience for operators with different dominant hand.

At 750, tissue can be resected and removed from the target site using one or more resection members mounted on the blade assembly. Examples of the resection members can include debrider, shaver, or shear, among others. In an example, the resection members can include a resection window and a rotatable resection member, as illustrated in FIG. 2. The resection window and the rotatable resection member can have respective resection surfaces, such as serrations, knife edges, toothed cutting blades, shearing blades, among other suitable cutting surfaces. The rotatable resection member can be driven by a motor to rotate axially within the interior of the inner tube, while the inner tube remains stationary. The motorized rotatable resection member can repetitively sweep across the resection window, and provide scissoring actions to excise tissue extending into the resection window between the respective resection surfaces of the resection window and the rotatable resection member.

In an example, the rotatable resection member can operate in an oscillation mode, such that the rotatable resection member can rotate in alternate directions (e.g., alternating between clockwise and counter-clockwise rotations) with respect to the resection window. In an example, the oscillation mode includes approximately 6-8 rotations in each direction. The resection window is thus referred to as an "outer blade", and the rotatable resection member 114 referred to as an "inner blade". The resected tissue can be collected into an interior of the inner tube, and withdrawn through a tissue suction conduit within the inner tube and the hand piece coupled to a vacuum source or other aspiration device, which can apply suction pressure to extract the resected tissue. In some examples, during the tissue removal procedure, irrigation fluid can be introduced into the outer and inner blades and surrounding tissue via an irrigation conduit within the inner tube, or in the annular space between the inner tube and the outer tube of the blade assembly. The irrigation fluid can provide lubrication, cooling, and preventing tissue clogging, among other functions.

In some examples, the blade assembly are disposable after use. The blade assembly can be detached from the hand piece for replacement, or alternatively for maintenance (e.g., cleaning, sterilization, or repair). Maintenance or replacement request is processed at 760. If no maintenance or replacement is needed, then tissue resection can be continued at 750, or ended, according to the operator's professional judgment. Alternatively, if necessary, further adjustment of the resection members (e.g., resection window) can be performed at 740 to achieve a better resection position or orientation with respect to the target tissue site. If at 760 a maintenance of the removable hand piece is deemed necessary, or if the disposable hand piece needs to be removed and replaced, then at 770 the coupling assembly (e.g., the locking member) can be unlocked from the hand piece. For example, as illustrated in FIG. 5A, an operator may use the release buttons 542A-542B to engage the locking members 516A-516B, such as by pressing said release buttons to release the locking members from the respective locking receptacles. The blade assembly can then be disconnected from the hand piece at 780. The maintenance or replacement of the blade assembly can then be performed at 790. In an example, the blade assembly is disposable after first use. A replacement blade assembly can be reconnected to the hand piece in accordance with previously described step 710.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical device for surgically removing tissue, comprising:
    a hand piece;
    a blade assembly removably attachable to the hand piece, the blade assembly including:
        a rotatable resection member configured to rotate and surgically remove tissue from a target tissue site; and
    a coupling assembly including a blade assembly locking member configured to:
        detachably couple the blade assembly to the hand piece;
        operatively enable or disable a rotation of the blade assembly relative to the hand piece, the rotation of the blade assembly causing a change in rotating angle of the blade assembly relative to the hand piece; and
        secure the rotating angle of the blade assembly,
        wherein the coupling assembly includes a first rotatable hub configured to be manually activated to cause the change in rotating angle of the blade assembly relative to the hand piece,
        wherein the hand piece includes an actuator configured to be manually activated, separately and independently of the manual activation of the first rotatable hub, to cause a change in orientation of a resection window on the blade assembly to expose the rotatable resection member.

2. The medical device of claim 1, wherein the rotatable resection member includes at least one of:
    a shaver;

a blade;
a burr; or
a debrider.

3. The medical device of claim 1, wherein the blade assembly includes an elongate body comprising:
an outer tube; and
an inner tube housed within the outer tube and rotatable relative thereto, the inner tube having the resection window to expose the rotatable resection member;
wherein the resection window and the rotatable resection member cooperate to shear tissue extending into the resection window.

4. The medical device of claim 3, wherein the rotatable resection member is configured to be driven by a motor to rotatably open and close the resection window to shear tissue extending between a first resection surface of the resection window and a second resection surface of the rotatable resection member.

5. The medical device of claim 4, wherein the rotatable resection member is configured to operate in an oscillation mode to rotate in alternate directions with respect to the resection window.

6. The medical device of claim 3, wherein the first rotatable hub is configured to be coupled to the outer tube of the blade assembly, wherein a rotation of the first rotatable hub causes a rotation of the outer tube to cause the change in rotating angle of the blade assembly relative to the hand piece; and
wherein the coupling assembly further includes a second rotatable hub coupled to the inner tube of the blade assembly, wherein a rotation of the second rotatable hub causes a rotation of the inner tube and a change in an orientation of the resection window with respect to the target tissue site.

7. The medical device of claim 6, wherein the blade assembly locking member includes:
a body;
at least one graspable tab attached to the body; and
an end portion extending from the body, the end portion configured (1) to be operatively received in one of a plurality of locking receptacles to disable the rotation of the outer tube and to secure the blade assembly at a specific rotating angle relative to the hand piece, or (2) to be operatively disengaged from the one of the plurality of locking receptacles to enable the rotation of the outer tube and the change in rotating angle of the blade assembly relative to the hand piece.

8. The medical device of claim 7, wherein the at least one graspable tab is operatively pressed to disengage the end portion from a first locking receptacle, or is operatively released to engage the end portion into a second locking receptacle.

9. The medical device of claim 3, wherein the hand piece includes a first one or more ports open to a lumen of the inner tube or an annular space between the inner tube and the outer tube, the first one or more ports configured to receive irrigation fluid to irrigate the rotatable resection member.

10. The medical device of claim 3, wherein the hand piece includes a second one or more ports open to a lumen of the inner tube, the second one or more ports operatively coupled to a vacuum source configured to apply suction pressure to withdraw resected tissue from the target tissue site.

11. A medical device for surgically removing tissue, comprising:
a hand piece; and
a blade assembly removably attachable to the hand piece, the blade assembly including:
a rotatable resection member configured to rotate and surgically remove tissue from a target tissue site;
a coupling assembly including a blade assembly locking member configured to:
detachably couple the blade assembly to the hand piece;
operatively enable or disable a rotation of the blade assembly relative to the hand piece, the rotation of the blade assembly causing a change in rotating angle of the blade assembly relative to the hand piece; and
secure the rotating angle of the blade assembly;
an outer tube; and
an inner tube housed within the outer tube and rotatable relative thereto, the inner tube having a resection window to expose the rotatable resection member, wherein the resection window and the rotatable resection member cooperate to shear tissue extending into the resection window;
wherein the blade assembly locking member comprises:
a body;
at least one graspable tab attached to the body; and
an end portion extending from the body, the end portion configured (1) to be operatively received in one of a plurality of locking recesses circumferentially located on a tubular housing portion of the hand piece to disable a rotation of the blade assembly relative to the hand piece and to secure the blade assembly at a specific rotating angle relative to the hand piece, and (2) to be operatively disengaged from the one of the plurality of locking recesses to enable the rotation of the blade assembly and to change the rotating angle of the blade assembly relative to the hand piece;
wherein the coupling assembly includes a first rotatable hub configured to be manually activated to cause the change in rotating angle of the blade assembly relative to the hand piece, the first rotatable hub configured to be coupled to the outer tube of the blade assembly, wherein a rotation of the first rotatable hub causes a rotation of the outer tube to cause the change in rotating angle of the blade assembly relative to the hand piece; and
wherein the coupling assembly further includes a second rotatable hub coupled to the inner tube of the blade assembly, wherein a rotation of the second rotatable hub causes a rotation of the inner tube and a change in an orientation of the resection window with respect to the target tissue site.

12. The medical device of claim 11, wherein the plurality of locking recesses are uniformly spaced around an outer circumference of the tubular housing portion of the hand piece.

13. The medical device of claim 11, wherein the plurality of locking recesses include at least five recesses circumferentially located on the tubular housing portion of the hand piece.

14. A medical device for surgically removing tissue, comprising:
a hand piece; and
a blade assembly removably attachable to the hand piece, the blade assembly including:
a rotatable resection member configured to rotate and surgically remove tissue from a target tissue site; and
a coupling assembly including:
a blade assembly locking member configured to:

detachably couple the blade assembly to the hand piece;

operatively enable or disable a rotation of the blade assembly relative to the hand piece, the rotation of the blade assembly causing a change in rotating angle of the blade assembly relative to the hand piece; and secure the rotating angle of the blade assembly relative to the hand piece; and a rotatable hub configured to be rotated to cause a change in an orientation of a resection window on the blade assembly to expose the rotatable resection member, wherein the hand piece includes an actuator adapted to engage and rotate the rotatable hub to change the orientation of the resection window.

15. The medical device of claim 14, wherein the actuator includes:

a thumbwheel; and a gear assembly including a worm coupled to the thumbwheel via a shaft of the worm, and a worm wheel meshing with the worm and engaging the rotatable hub;

wherein a rotation of the thumbwheel causes the change in the orientation of the resection window via the gear assembly and the rotatable hub.

16. The medical device of claim 15, wherein the gear assembly is configured to:

transmit a forward rotation of the thumbwheel towards a distal end of the blade assembly into a first direction of rotation of the resection window; and transmit a backward rotation of the thumbwheel towards a proximal end of the blade assembly into a second direction, opposite the first direction, of rotation of the resection window.

17. The medical device of claim 15, wherein the actuator includes two thumbwheels laterally disposed on opposite sides of a tubular housing portion of the hand piece, the two thumbwheels coupled to the gear assembly at opposite terminals of the worm shaft.

* * * * *